(12) United States Patent
Heumann et al.

(10) Patent No.: US 7,099,435 B2
(45) Date of Patent: Aug. 29, 2006

(54) HIGHLY CONSTRAINED TOMOGRAPHY FOR AUTOMATED INSPECTION OF AREA ARRAYS

(75) Inventors: John M. Heumann, Loveland, CO (US); Colin Fox, Auckland (NZ); David Gines, Ft. Collins, CO (US); Nicholas Tufillaro, San Francisco, CA (US)

(73) Assignee: Agilent Technologies, Inc, Palo Alto, CA (US)

( * ) Notice: Subject to any disclaimer, the term of this patent is extended or adjusted under 35 U.S.C. 154(b) by 0 days.

(21) Appl. No.: 10/714,321

(22) Filed: Nov. 15, 2003

(65) Prior Publication Data

US 2005/0105682 A1    May 19, 2005

(51) Int. Cl.
*G01N 23/083* (2006.01)

(52) U.S. Cl. .......................................... 378/58; 378/22
(58) Field of Classification Search ................ 378/4, 378/8, 21, 22, 23, 51, 58, 62, 901
See application file for complete search history.

(56) References Cited

U.S. PATENT DOCUMENTS

| | | | |
|---|---|---|---|
| 4,926,452 A | 5/1990 | Baker et al. | |
| 5,081,656 A | 1/1992 | Baker et al. | |
| 5,097,492 A | 3/1992 | Baker et al. | |
| 5,259,012 A | 11/1993 | Baker et al. | |
| 5,321,613 A * | 6/1994 | Porter et al. | 702/1 |
| 6,002,739 A | 12/1999 | Heumann | |
| 6,201,850 B1 | 3/2001 | Heumann | |

OTHER PUBLICATIONS

A. Louis and F. Natterer, "Mathematical Problems of Computerized Technology", Proc. IEEE 71:379-389 (1983).

K. Hanson and G. Wecksung, "Bayesian Approach to Limited-angle Reconstruction in Computed Tomography", J. Optimal Sci. Am. 73:1501-1509 (1983).

S. German and D. McClure, "Bayesian Image Analysis: An Application to Single Proton Emission Tomography", Proc. Statist. Comput. Sect. Amer. Stat. Soc. Washington, D.C., paragraph. 12-18 (1985).

T. Herbert and R. Leah, "A Generalized EM Algorithm for 3-D Bayesian Reconstruction From Poisson Data Using Gibbs Priors", IEEE Trans. on Medical Imaging 8:194-202 (1989).

P.J. Green, "Bayesian Reconstruction From Emission Tomography Data Using A Modified EM Algorithm", IEEE Trans. on Medical Imaging 9:84-93 (1990).

K. Sauer and C.A. Bouman, "A Local Update Strategy For Iterative Reconstruction From Projections", IEEE Trans. On Signal Processing 41:534-548 (1993).

P. Green, "Reversible Jump Markov Chain Monte Carlo Computation And Bayesian Model Determination", Biometrica 82:711-732 (1995).

(Continued)

*Primary Examiner*—David V Bruce

(57) ABSTRACT

A tomographic reconstruction method and system incorporating Bayesian estimation techniques to inspect and classify regions of imaged objects, especially objects of the type typically found in linear, areal, or 3-dimensional arrays. The method and system requires a highly constrained model M that incorporates prior information about the object or objects to be imaged, a set of prior probabilities P(M) of possible instances of the object; a forward map that calculates the probability density P(D|M), and a set of projections D of the object. Using Bayesian estimation, the posterior probability p(M|D) is calculated and an estimated model $M_{EST}$ of the imaged object is generated. Classification of the imaged object into one of a plurality of classifications may be performed based on the estimated model $M_{EST}$, the posterior probability p(M|D) or MAP function, or calculated expectation values of features of interest of the object.

58 Claims, 8 Drawing Sheets

OTHER PUBLICATIONS

B. Ohnesorge, T. Flohr, K. Klingenbeck-Regn, "Efficient Object Scatter Correction Algorithm For Third and Fourth Generation CT Scanners", Eur. Radiol. 9, 563-569 (1999).

T. Freese, C. Bouman, and K. Sauer, "Multiscale Bayesian Methods for Discrete Tomography", Discrete Tomography: Foundations, Algorithms, and Applications, edited by G. Herman and A. Kuba, Birkhauser Boston, Cambridge, MA, pp. 237-261 (1999).

C. Fox and G. Nicholls, "Exact MAP States and Expectations from Perfect Sampling: Grieg, Porteous, and Scheult Revisited", in Bayesian Inference and Maximum Entropy Methods in Science and Engineering, edited A. Djafari, AIP Conference Proceedings, 568:252-263 (2001).

J. Lui and C. Sabatti, "Generalised Gibbs sampler and multigrid Monte Carlo for Bayesian computation", Biometrika 87:353-369 (2000).

* cited by examiner

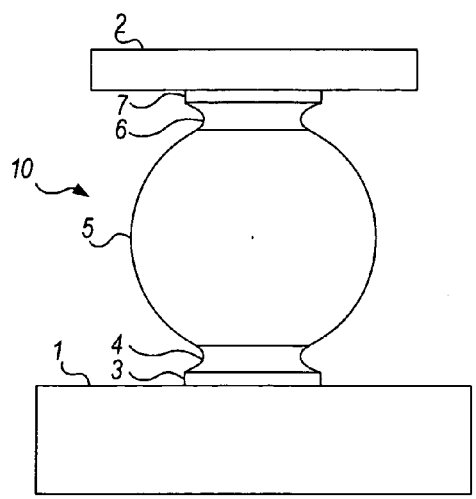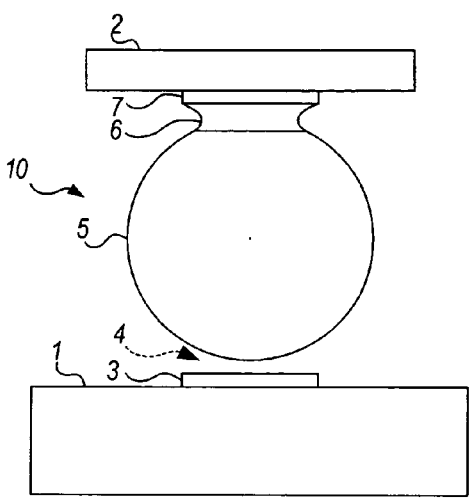
FIG. 1     FIG. 2
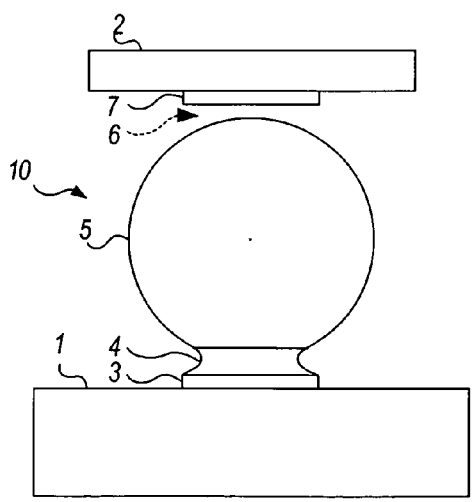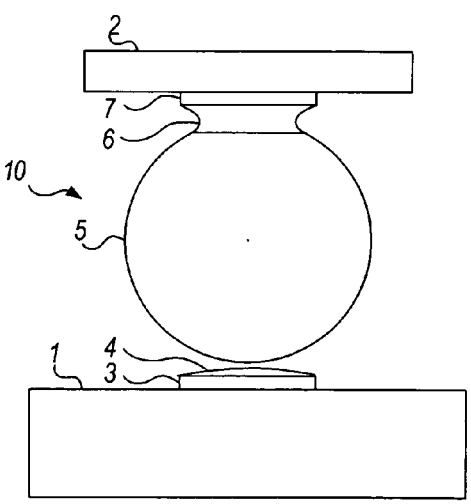
FIG. 3     FIG. 4

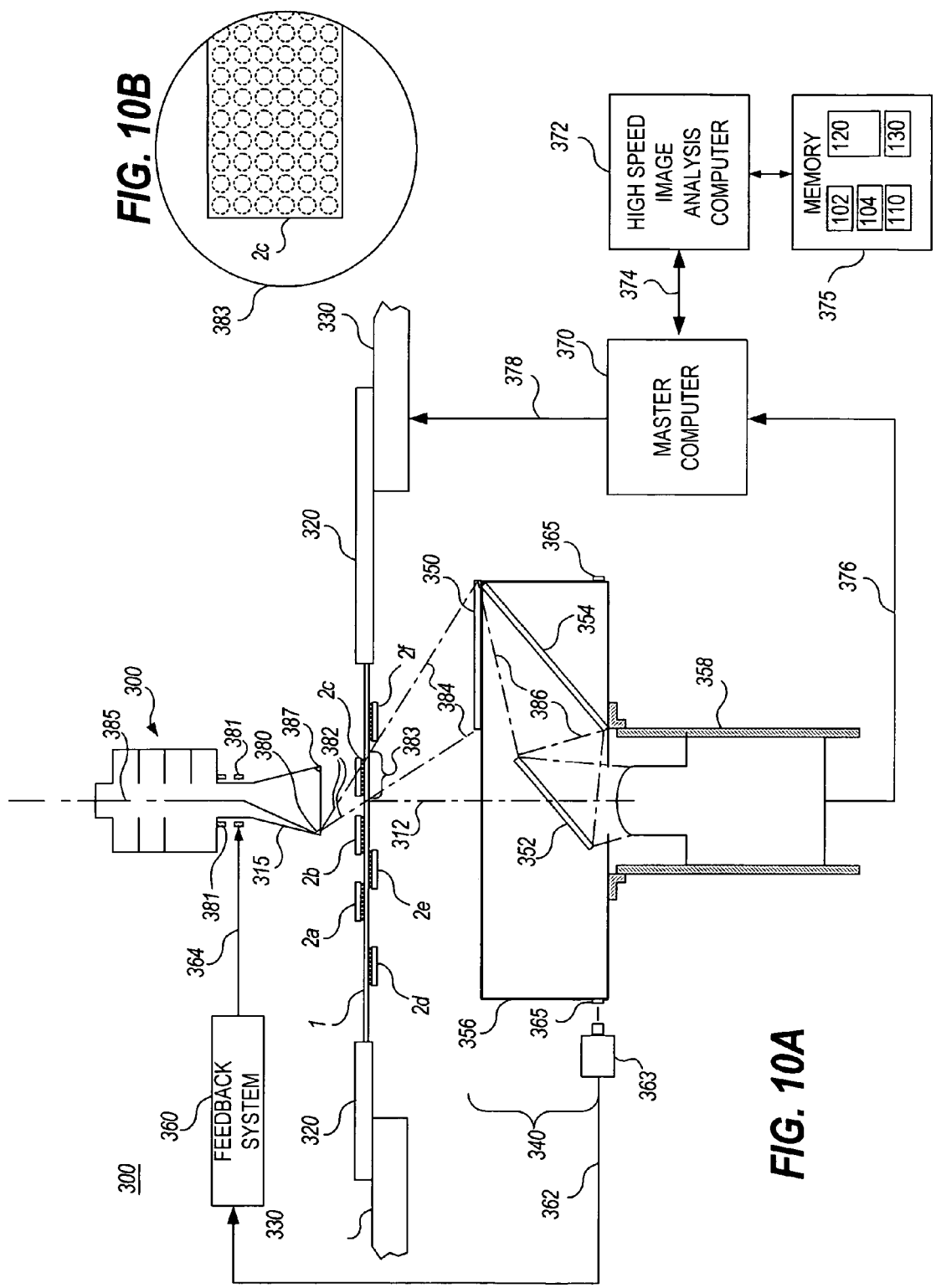

HIGHLY CONSTRAINED TOMOGRAPHY FOR AUTOMATED INSPECTION OF AREA ARRAYS

BACKGROUND OF THE INVENTION

The present invention relates generally to automated imaging inspection techniques, and more particularly to automated inspection of arrays of identical objects using highly constrained tomography and Bayesian estimation.

Tomographic reconstruction from projections provides cross-sectional and 3-dimensional information, and is utilized in many fields including medical imaging, security screening, and automated inspection of manufactured goods. In manufacturing electronic assemblies, for example, solder joints or other interconnects are often not accessible for electrical testing or optical inspection. As a result, imaging using penetrating radiation, e.g. X-rays, is often used for automated inspection of such joints. Tomographic or 3-dimensional methods are required for two reasons. First, modern printed circuit assemblies (PCAs) are typically double-sided, and, in addition, may possess multiple internal layers. As a result, joints or components frequently obscure other joints in transmission radiographs, preventing easy interpretation. Second, many joint types are themselves 3-dimensional in nature, making it difficult or impossible to distinguish good joints from bad joints in transmission radiographs. In addition to their 3-dimensional nature, these joint types are typically deployed in dense arrays (linear, areal, or even 3-dimensional) with large numbers of similar joints in close proximity.

Tomographic methods which have been applied to automated X-ray inspection of solder joints include laminography, tomosynthesis, and various forms of cone beam or fan beam computed tomography (CT). CT methods include filtered backprojection (also known as convolution backprojection) as well as other transform methods, iterative methods including conjugate gradients, and specialized variations of these techniques. Unfortunately, such conventional methods typically perform poorly when applied to arrays of 3-dimensional solder joints, leading to sever artifacts in the reconstructed images that impede interpretation and automatic classification. Among the cause of such artifacts are poor signal to noise ratio (SNR), limited projection angles, lack of linearity, and X-ray scattering.

Solder joints typically contain lead, tin, or both, and are highly attenuating for X-rays. Each joint in an array can be up to several millimeters thick, attenuating more than 99% of the incoming X-ray photons, and resulting in a very low SNR in regions of greatest interest. Additionally, angles at which projection data may be collected are severely limited by nearby joints which are similarly highly attenuating. Equatorial projections are not available, for example, since each ray would typically pass through a large number of joints. Axial projections with acceptable SNR may also be difficult or impossible to obtain at reasonable doses (e.g., for CGAs or similar joints which are longest in the axial direction). As a result, projections are often available only for a limited range of angles approximately 30°–60° off the axial direction. The well-known Radon inversion theorem (See A. Louis and F. Natterer, "Mathematical Problems of Computerized Tomography", $Proc.$ $IEEE$ 71:379–389 (1983)) guarantees that an object can be reconstructed from noiseless projections from all possible angles. When projections from a limited range of angles are available, or are corrupted by noise, exact reconstruction is not possible in the absence of additional information.

High attenuation combined with the use of a polychromatic source also leads to difficulties with reconstruction. Transmission tomography generally assumes exponential attenuation, $1/l_0 = e^{-\lambda X}$, where $l_0$ and $l$ are the original and attenuated intensities, respectively, $\lambda$ is a linear attenuation coefficient, and X is the distance traveled through the object. Under these assumptions, taking logarithms leads to a linear system: $-\log(l) = -\log(l_0) + \lambda X$. X-ray sources used for solder joint inspection are broad-band, often emitting X-rays ranging in energy from 10 keV up to 160 keV or more. The attenuation coefficient, $\lambda$, is not constant over this range, and instead must be treated as a function of energy, with various materials having characteristic spectra. This poses two closely related difficulties for standard methods of tomographic reconstruction. First, the system equations cannot be readily linearized, violating the assumptions underlying all common tomographic methods. Second, as the beam passes further into the sample, the effective spectrum changes as radiation at some energies is preferentially absorbed or scattered. Typically, lower energies and energies near absorption edges are attenuated more strongly, resulting in so-called "beam hardening". The net result is that identical absorbers at different locations can produce different attenuation, again violating the assumptions underlying tomography.

In addition, all classical methods of tomography, both transmission and emission, are predicated on straight-line propagation from source to detector, forming projections of the object under test. A significant minority of X-rays, however, is deflected during propagation through a sample. Both elastic and inelastic scattering occur, resulting in changes in direction (or equivalently, absorption followed by emission in a different direction), with or without an associated change of energy. Inelastic scattering, for example, is prominent in low-Z materials such as the glass-epoxy composites typically used as substrates for printed circuit assemblies. While the fraction of incoming photons undergoing inelastic scattering is typically small, they can nonetheless represent a large percentage of the detected X-rays in dark regions, as when a low-Z material such as a PCB substrate is adjacent to a highly attenuating material such as a solder joint. Scattering is particularly troublesome when area array sensors are used, since collimation is typically not practical. Heuristic corrections for scatter and beam hardening have been proposed, and can reduce, but not eliminate artifacts resulting from these mechanisms (e.g., see B. Ohnesorge, T. Flohr, K. Klingenbeck-Regn, "Efficient Object Scatter Correction Algorithm For Third and Fourth Generation CT Scanners", $Eur.$ $Radiol.$ 9, 563–569 (1999)).

In principle, Bayesian reconstruction methods can surmount these difficulties. As a brief overview of the principles of the Bayesian tomography, let D represent a set of measured projection data, and let M represent a model of the object under consideration. Typically, M consists of a set of parameters describing the object(s) of interest. The goal is to assign values to the parameters of M that accurately reflect the objects being inspected from the noisy and potentially incomplete data, D. In maximum likelihood (ML) estimation, the estimated model $M_{ML}$ is taken to be the value of M which maximizes the likelihood, P(D|M), of observing D, assuming M is correct. Equivalently, and more commonly, the log-likelihood can be maximized. Under appropriate assumptions, each of the classical tomography methods is equivalent to a form of maximum likelihood estimation.

In contrast, Bayesian estimation incorporates additional a priori or prior information, p(M), about the model M, summarizing all objective and subjective information about how likely alternative models are thought to be in the absence of measured data, D. The posterior probability, p(M|D), for any particular model (i.e., the probability that a given model M is correct having observed data set D) can be calculated using Bayes' rule, p(M|D)=p(D|M)p(M)/p(D), where p(D)=∫p(D|M)p(M) serves as a normalization constant.

In the simplest form of Bayesian analysis, so-called maximum "a posteriori" or MAP estimation, the estimated model $M_{MAP}$ is taken to be the value of M which maximizes p(D|M)p(M). The normalizing factor, p(D), is not required, since it is not a function of M. MAP estimation generalizes maximum likelihood by incorporation of prior information, and this has been shown effective in reducing artifacts in tomographic reconstruction. (See S. Geman and D. McClure, "Bayesian Image Analysis: An Application to Single Photon Emission Tomography", *Proc. Statist. Comput. Sect. Amer. Stat. Soc.* Washington, D.C., paragraph. 12–18 (1985); T. Hebert and R. Leah, "A Generalized EM Algorithm for 3-D Bayesian Reconstruction From Poisson Data Using Gibbs Priors", *IEEE Trans. on Medical Imaging* 8:194–202 (1989); P. J. Green, "Bayesian Reconstruction From Emission Tomography Data Using A Modified EM Algorithm", *IEEE Trans. on Medical Imaging* 9:84–93 (1990); K. Sauer and C. A. Bouman, "A Local Update Strategy For Iterative Reconstruction From Projections", *IEEE Trans. On Signal Processing* 41:534–548 (1993); and K. Hanson and G. Wecksung, "Bayesian Approach to Limited-angle Reconstruction in Computed Tomography", *J. Optimal. Sci. Am.* 73:1501–1509 (1983), each of which is incorporated herein by reference for all that it teaches). Iterative methods to increase posterior probability, p(M|D), are typically used, sometimes using a filtered backprojection reconstruction as a starting estimate. MAP methods are also available for discrete tomography, where one or more model parameters (e.g., the attenuation coefficient in a particular region) are to be chosen from among a finite and typically small number of choices.

Considerable effort has been devoted to developing methods that converge rapidly, some requiring differentiable likelihoods and others which do not. Multi-resolution analysis has been shown to speed convergence and solution quality in some cases. (See T. Freese, C. Bouman, and K. Sauer, "Multiscale Bayesian Methods for Discrete Tomography", *Discrete Tomography: Foundations, Algorithms, and Applications*, edited by G. Herman and A. Kuba, Birkhauser Boston, Cambridge, Mass., pp. 237–261 (1999), incorporated herein by reference for all that it teaches). In multi-resolution analysis, prior information has typically been incorporated via a potential function or Markov random field penalizing neighboring pixel values which are thought to be unlikely (e.g., a sharp difference not lying along well defined edges).

Both ML and MAP estimation result in a single model for the reconstructed object, namely that model which maximizes, respectively, the likelihood or the posterior probability. This can be appropriate and effective when the corresponding function (likelihood or posterior probability) is symmetrical or sharply peaked at the maximum. It can, however, be very misleading with distributions that do not satisfy these assumptions. (See C. Fox and G. Nicholls, "Exact MAP States and Expectations from Perfect Sampling: Grieg, Porteous, and Scheult Revisited", in *Bayesian Inference and Maximum Entropy Methods in Science and Engineering*, edited by A. Djafari, *AIP Conference Proceedings*, 568:252–263 (2001), incorporated herein by reference for all that it teaches).

Full Bayesian inference, as opposed to MAP estimation, avoids this problem by treating the posterior probability, p(M|D), as a distribution over all possible models. Quantities of interest, such as parameter values or utility functions, are estimated by taking expectations over the posterior probability. In rare cases, the posterior probability and associated expectations may be computed analytically. More typically, numerical approximation is required. Markov Chain Monte Carlo (MCMC) methods represent the current state-of-the-art for approximating such expectations. Discrete and continuous parameters may be freely mixed, and differentiable likelihood is not required. As in the case of MAP estimation, multi-resolution analysis may be applied in conjunction with MCMC methods to improve convergence.

Full Bayesian analysis incorporating calculations of expectations (e.g., using MCMC) is computationally demanding compared to MAP estimation, which in turn is often slower and more demanding than conventional tomography. A key factor in successful implementation of full Bayesian tomography is therefore careful choice of a framework in which prior knowledge can be naturally and effectively represented, and in which MCMC approximation converges rapidly.

In order to illustrate some of the limitations and difficulties when attempting to use conventional model representations with Bayesian tomography, consider a specific example from the field printed circuit inspection. FIG. 1 shows a stylized cross-section through an ideal ball grid array (BGA) joint 10 connecting a printed circuit board (PCB) pad 3 of a printed circuit board (PCB) 1 to an integrated circuit (IC) pad 7 of integrated circuit (IC) 2. As shown, BGA joint 10 includes a ball 5 soldered to the PCB pad 3 with solder fillet 4 and soldered to the IC pad 7 with solder fillet 6.

In addition to normal joints, several types of defective joints can occur. FIGS. 2 and 3 respectively show a cross-section of a defective BGA joint where the PCB interface solder fillet 4 and IC interface solder fillet 6 are missing. Another defect that can occur is insufficient solder at fillet 4 (as shown in FIG. 4) or 6 (not shown), which is especially problematic when the ball 5 is of the non-collapsible type. Further, excessive solder can result in a short between one or more neighboring joints.

The simplest representation for reconstruction of a 3-dimensional region is a uniform voxelation. A BGA joint 10, for example, might be divided into 15×15×15 cubical voxels of uniform size, as illustrated in FIG. 5. In the simplest, and most conventional use of such a representation, fitting the model, M, for a single BGA joint involves assigning a value of the so-called CT number, λX, at each of the 3,375 voxels. Such a voxel-based model is an example of what is typically called a low-level representation. Voxel based models are extremely general and capable of representing virtually any object. Bayesian tomography generally requires computing the likelihood that projection images, D, could result from a given model, M. This computation is straightforward when a voxel-based model is used. Simple, deterministic ray-tracing can be used to predict the projections that would result in the absence of noise. Noise of known distribution may then be added, completing the calculation of the likelihood.

Despite these advantages, voxel-based, and other low-level representations are often poorly suited for Bayesian tomography. The number of parameters to be fitted is large, and may exceed the number of measurements, particularly when the number of projections is limited, as in X-ray PCA inspection. The resulting system of equations is typically ill-conditioned and often inconsistent, leading to slow convergence and artifacts in the fitted model. Local maxima are also common, since the system equations are not truly linear. Additionally, constraints and prior knowledge can be difficult or impossible to express in such a representation. Local information, e.g. smoothing or other regularization, can be easily incorporated, but global information is problematic. BGA balls are approximately spherical with diameters falling predominantly in a narrow range, for example, and the spacing between joints is known in advance. Unfortunately, expressing this information in a low-level representation is difficult and inefficient.

As described above, Bayesian reconstruction can minimize the effects of limited or poor data by incorporating prior information. Additionally, a detailed forward map accurately reflecting image formation and noise statistics replaces the often inappropriate and numerically unstable inverse map used by conventional methods. Nonetheless, Bayesian methods have found limited use to date in tomographic reconstruction, particularly in realtime automated industrial imaging inspection applications where the inspection and analysis operations must keep up with the rate of the particular manufacturing line, for example in electronic assembly manufacturing and/or testing lines. This is due both to the need to understand and model the relevant processes in considerable detail, including relevant prior knowledge, and to the high computational demands of Bayesian inference. Further, representation of prior knowledge and constraints is often difficult in conventional voxel-based representations.

It would therefore be desirable to have a computationally tractable framework for practical exploitation of the benefits of Bayesian reconstruction in industrial imaging that incorporates prior knowledge in a clear, concise, and natural fashion, and which is computationally efficient and robust. It would also be desirable that such framework allow realtime inspection, analysis, and classification in an automated industrial imaging inspection environment, especially one where the object(s) to be inspected consist of dense arrays of similar objects.

SUMMARY OF THE INVENTION

The invention is a novel method and system for use in industrial imaging applications such as automated inspection of imaged objects, especially objects of the type typically found in linear, areal, or 3-dimensional arrays. Bayesian techniques for tomographic reconstruction are combined with a highly-constrained object representation to inspect and classify regions of imaged objects.

The method and system requires a set of "projections" (i.e., observed image data) D taken of an object to be classified, a highly constrained model, M, of the object(s) to be imaged, a set of prior probabilities P(M) over possible models, and a forward map for computing the likelihood P(D|M) of the projections D given possible instances of the model M.

Bayesian techniques are used to estimate a model, $M_{EST}$, that best fits the observed data D. In an example embodiment, MAP estimation is utilized to estimate the model, $M_{EST}=M_{MAP}$, that maximizes posterior probability or a derived objective function. In the alternative, or in addition, expectations of features or quantities of interest, including decision theoretic utility functions, may be calculated, for example, using a Markov Chain Monte Carlo (MCMC) algorithm.

The estimated model $M_{EST}$, posterior probability distribution, and/or calculated expectations may then be used to automatically classify the imaged object(s) according to two or more classifications (e.g. pass/fail) using standard techniques from statistical pattern classification and decision theory.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein:

FIG. 1 is a stylized cross-sectional side view of an ideal ball grid array (BGA) joint;

FIG. 2 is a cross-sectional side view of a defective BGA joint where the PCB interface solder fillet is missing;

FIG. 3 is a cross-sectional side view of a defective BGA joint where the IC interface solder fillet is missing;

FIG. 4 is a cross-sectional side view of a defective BGA joint where insufficient solder is present at the PCB interface;

FIG. 10A is a schematic diagram of an acquisition apparatus used in accordance with the invention for collecting and analyzing projections of an object of interest;

FIG. 10B shows a top view enlargement of an inspection region shown in FIG. 10A;

DETAILED DESCRIPTION

1. General Embodiment of the Invention

Figure 6:
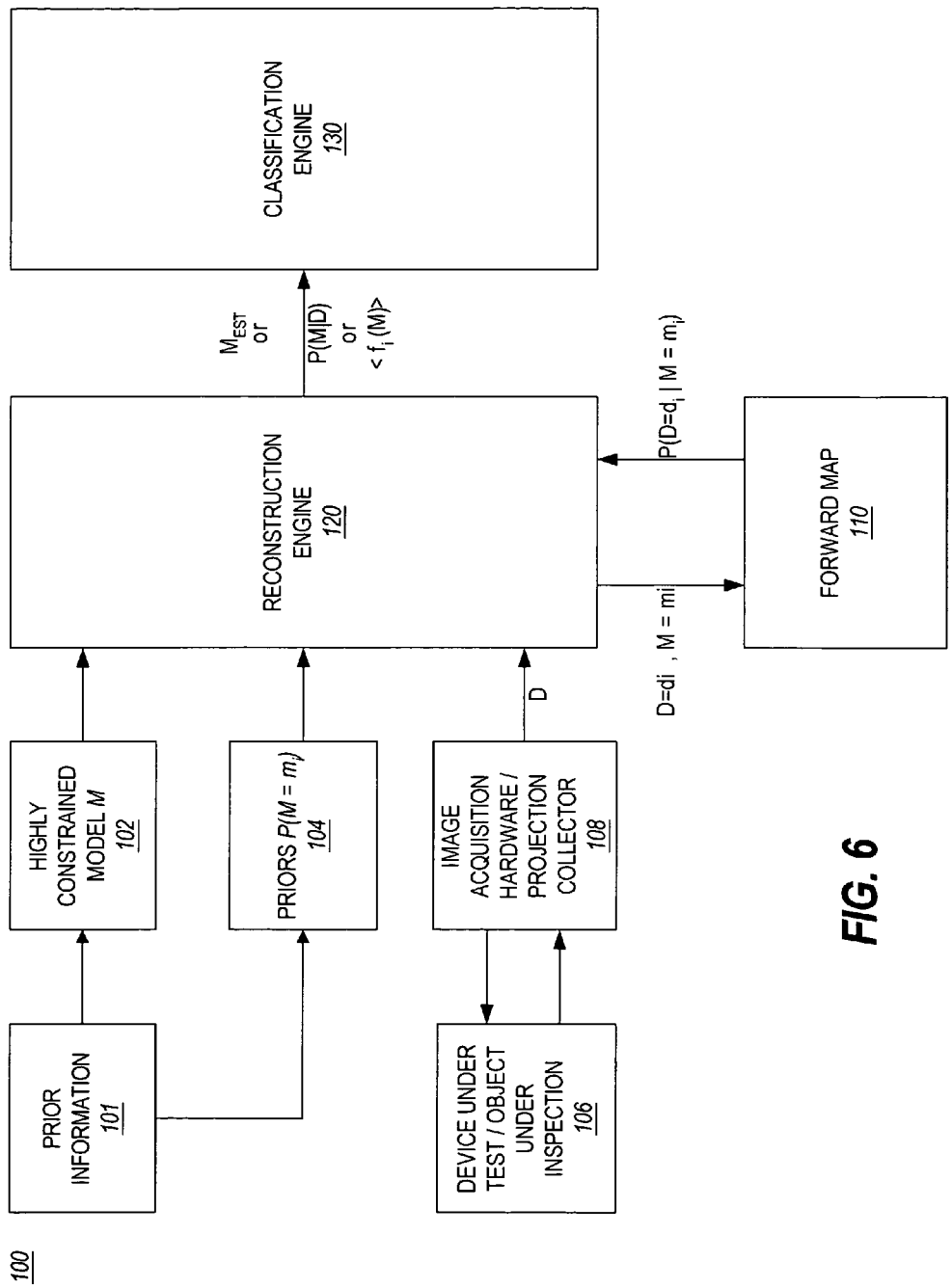
FIG. 6 is a block diagram of an automated imaging inspection system implemented in accordance with the invention.

Turning now to implementation of the present invention, FIG. 6 shows a block diagram of an automated imaging inspection system 100 in accordance with the invention. As shown therein, the automated imaging inspection system 100 includes a reconstruction engine 120 that reconstructs or estimates an object from a set of projections D of an object under inspection on a device under test 106 that are collected by imaging hardware 108 given a highly constrained model M 102 that is constrained by a set of prior information 101, a set of prior probabilities (or "priors") P(M) 104, and a forward map 110. As used herein, the term "projections" refers to a set of observations of an object of interest in the form of any type of image modality, where each observation is taken from a different viewpoint. In the illustrative embodiment, the projections are in the form of X-ray images of the object of interest.

The reconstruction engine 120 may be configured to generate one or more of three different outputs. These outputs include an estimated model $M_{EST}$, the posterior probability P(M|D), and/or expectation values <$f_i$(M)> of parameters or functions of interest using Bayesian reconstruction analysis. A classification engine 130 classifies the reconstructed or estimated object into one or more classes based on the output(s) from the reconstruction engine 120.

The reconstruction engine 120 requires a highly constrained model, M, 102 for an object of interest to be inspected. Parametric representations (e.g., $M=m_i=\{\pi_1, \pi_2, \ldots, \pi_n\}$) are preferably used, although not required. Discrete and continuous variables may be freely intermixed. The model M 102 is constrained using prior information 101 about the object of interest to be inspected. The prior information 101 can be anything known about the object to be inspected, including all available objective and subjective information. For example, if the device under test 106 is a printed circuit board, prior information includes knowledge that the object to be imaged may include a component, a component leg, a BGA joint, a CGA joint, a trace, a via, etc. The prior information can also include physical constraints, such as the positivity of X-ray attenuation, and/or preferences of a domain expert.

Figure 13:
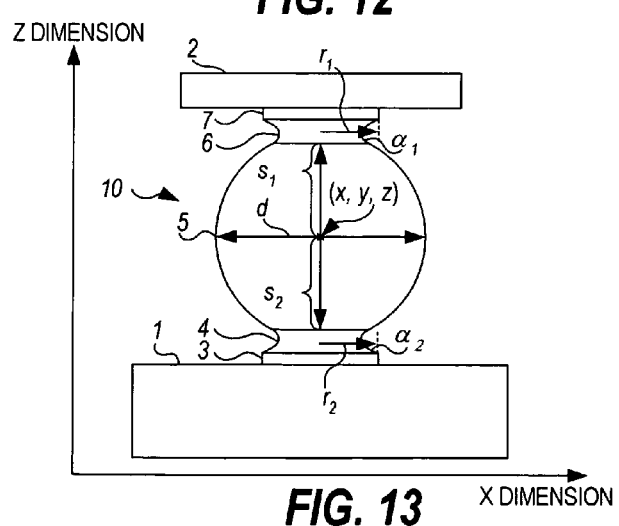
FIG. 13 is a cross-sectional side view of a single BGA joint of the ball grid array of FIG. 12, illustrating the x- and z-dimensions.

The present invention utilizes a mid- to high-level representation of the object to be inspected, in this example BGA joints, much the way a CAD description of a PCA would. A key property of the chosen representation is that each object can be defined by relatively few parameters possibly including location, orientation and scale. An example of such a representation is illustrated in FIG. 13 and is described in more detail below. Such an image representation has far fewer parameters than the prior art voxel-based representation discussed previously.

A set of prior probabilities, p(M) 104 for all possible instances of the object of interest is also required. The prior probabilities p(M) 104 summarize the prior information 101 including all objective and subjective information about how likely alternative models are thought to be in the absence of measured data. The prior probabilities p(M) 104 may be determined theoretically, subjectively, or by statistical sampling of representative instances.

Imaging hardware/projection collection apparatus 108 collects a set of projections $D=\{d_1, d_2, \ldots, d_m\}$ from the object of interest on the DUT 106. To this end, one or more of the source, detector, and/or object are configured in a first position and an image $D=d_1$ is acquired. One or more of the source, detector, and/or object is moved to another position and a second image $D=d_2$ is acquired. This process is repeated, moving one or more of the source, detector, and/or object and acquiring a corresponding image until a desired number n of images $D=\{(d_1, d_2, \ldots, d_n\}$ is acquired. The resulting set of images D therefore comprises a set of views each containing a different perspective of the object under inspection.

As described in the background section, the projections (or detected images) D will only approximate the mathematical definition of a projection operator since noise and other uncertainties are present in all real systems. For example, due to scattering, not all detected X-rays will have traveled in a straight line from source to detector.

Although the reconstruction engine 120 requires a set of projections D, it will be readily understood that imaging hardware 108 for collecting the projections D may be implemented in the apparatus of the invention itself, or alternatively may be acquired by a completely separate imaging system.

Forward map 110 computes the likelihood $P(D=d_i|M=m_i)$ of generating certain observed projections, $D=d_i$, if the object under inspection was accurately represented by model $M=m_i$. The forward map 110 must be capable of generating the likelihood $P(D=d_i|M=m_i)$ of any set of projections $D=d_i$ for all possible instances $M=m_i$ of the model M for the object under inspection.

Because various types of noise are always present in a real system, the forward map 110, P(D|M), will be non-deterministic, with a range of possible projections resulting from a specific instance of the object under inspection. In other words, the forward map 110 must include knowledge of the noise properties of the system of interest. A simple and effective method for computing the forward map is to generate a voxel-based or other low-level model from the particular instance of the constrained, high-level representation M. Deterministic projections may then be computed by ray-tracing (i.e., computationally calculating how much of the object a ray would pass through if the ray traveled in a straight line from the source to the detector). Finally noise of known distribution may be added to arrive at an estimate of the likelihood. Note that when used in this sense "noise" constitutes any difference between the predicted and actual projections, and can include systematic errors.

Alternatively, some or all of the stochastic processes present in the system, e.g. simulation of scatter, can be incorporated directly in the projection forming procedure, rather than modeled as additive noise. For maximum accuracy, a complete Monte Carlo simulation of the projection process would be used; however, such an implementation shall have to wait for improved processing speeds since such complete simulations are presently too time consuming for inclusion in the forward map in industrial inspection using current processing technologies.

The reconstruction engine 120 utilizes Bayesian techniques to estimate one or more of a) the best-fit model, $M_{EST}$, b) the posterior probability distribution over possible models, P(M|D), or c) expectations of quantities of interest, <$f_i$(M)>, over P(M|D). Quantities of interest will typically be discriminant or utility functions useful for classification, but can include any desired function of the model parameters. Bayesian estimation combines prior information, P(M), and measured results in an optimal fashion to arrive at these estimates. The posterior probability for any particular model can be calculated using Bayes' rule, $$P(M|D) = \frac{P(D|M)P(M)}{P(D)}, \text{ where } P(D) = \int_M P(D|M)P(M)$$

serves as a normalization constant. In the simplest form of Bayesian analysis, so-called "maximum a posteriori" or MAP estimation, the best estimate for the reconstruction is taken to be that particular model $M_{EST}=M_{MAP}$ that maximizes P(D|M)P(M) taken over all possible models of M. The reconstruction engine 120 visits model states $M=m_i$ with frequency proportional to posterior probability $P(M=m_i|D)$. By remembering the instance with the greatest posterior, $M_{EST}$ can be estimated. The posterior distribution itself, P(M|D), can be estimated, for example, by computing a histogram or kernel density estimate over the model states visited. Similarly, the expectation of a feature of interest, $f_j(M)$, can be estimated by adding $f_j(M=m_i)$ to a counter each time model state $m_i$ is visited, then dividing by the number of time periods (states) at the conclusion of the simulation. One or more of $M_{EST}$, P(M|D), and $<f_j(M)>$ can be estimated and returned as desired. This choice is governed primarily by the classification approach in use by classification engine 130, and by details of the specific application. If the posterior is found to generally be symmetric or sharply peaked in a specific application, for example, the MAP estimate, $M_{EST}=M_{MAP}$, suffices. An additional advantage of the highly constrained models M 102 used herein is that they tend to result in peaked, symmetric posteriors. Expectations of quantities of interest can be used even when the posterior does not satisfy the above conditions. Direct estimation of the posterior is seldom used for classification purposes, but can be helpful in initial investigation, particularly in selecting quantities whose expectations are to be estimated.

Figure 5:
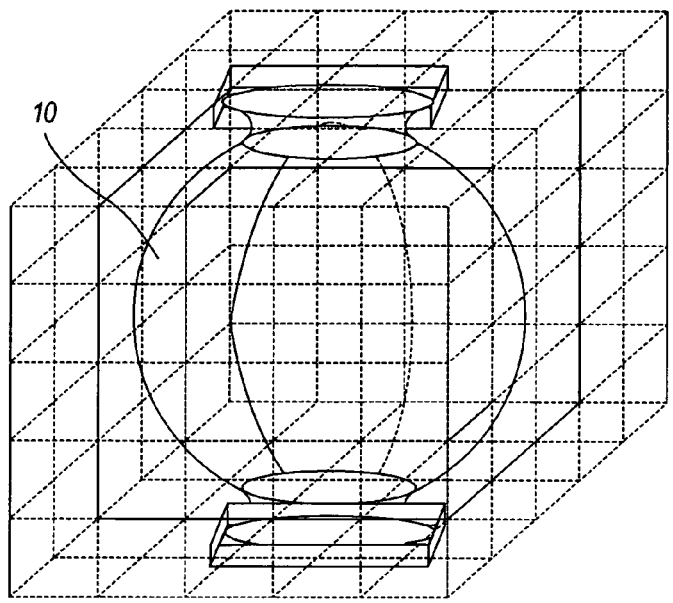
FIG. 5 is a prior art uniform voxel-based representation for reconstruction of a BGA joint.
Figure 7:
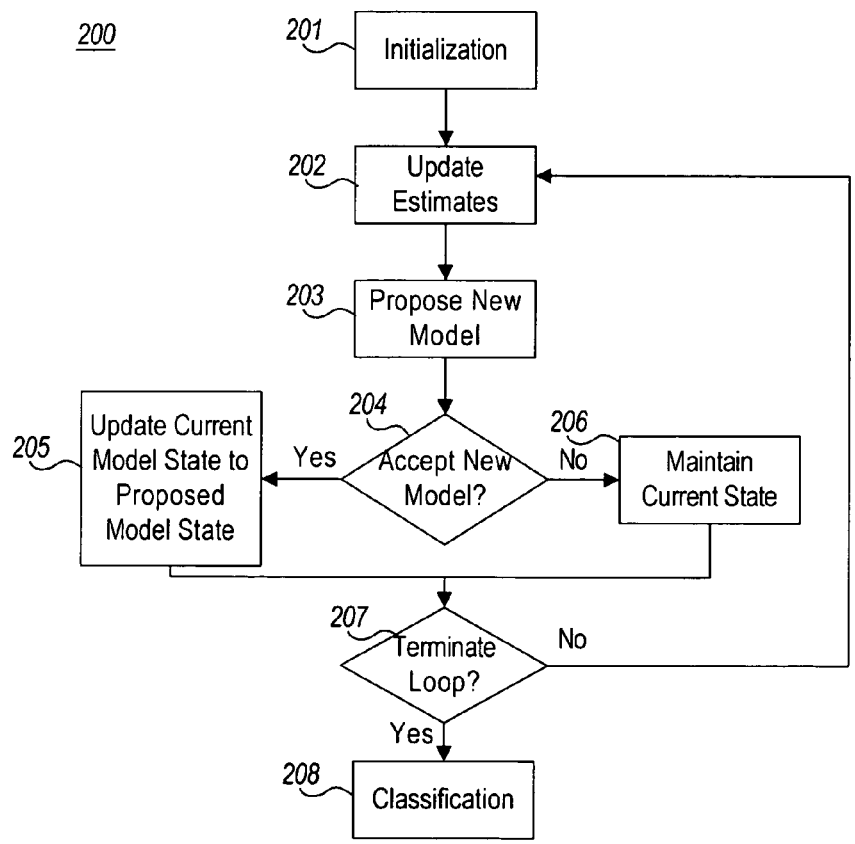
FIG. 7 is an operational flowchart of a high-level operational method performed by the reconstruction engine in FIG. 6.

FIG. 7 illustrates the high-level operational method 200 of the reconstruction engine 120. As shown therein, the reconstruction engine 120 performs initialization of state and estimation variables (step 201). Estimates are updated, or in the case of the first iteration through the loop, set to initial estimates (step 202). A new model state is then proposed (step 203). The new model state is accepted or rejected (step 204) according to a procedure described below. If accepted, the current model state is set to the proposed model state (step 205). If rejected, the proposed model state is discarded (step 206). A determination is made as to whether to terminate the updating loop (step 207), for example by determining whether sufficient precision has been obtained or if the allotted time or number of iterations have been exceeded. If termination is not selected, estimates are updated (step 202), and the loop including steps 202 through 207 is repeated until termination. Following termination of the update loop, estimates are updated to reflect the final state (not shown), and classification is performed (step 208, shown for completeness but using dashed lines because this step is performed by the classification engine 130).

Figure 8:
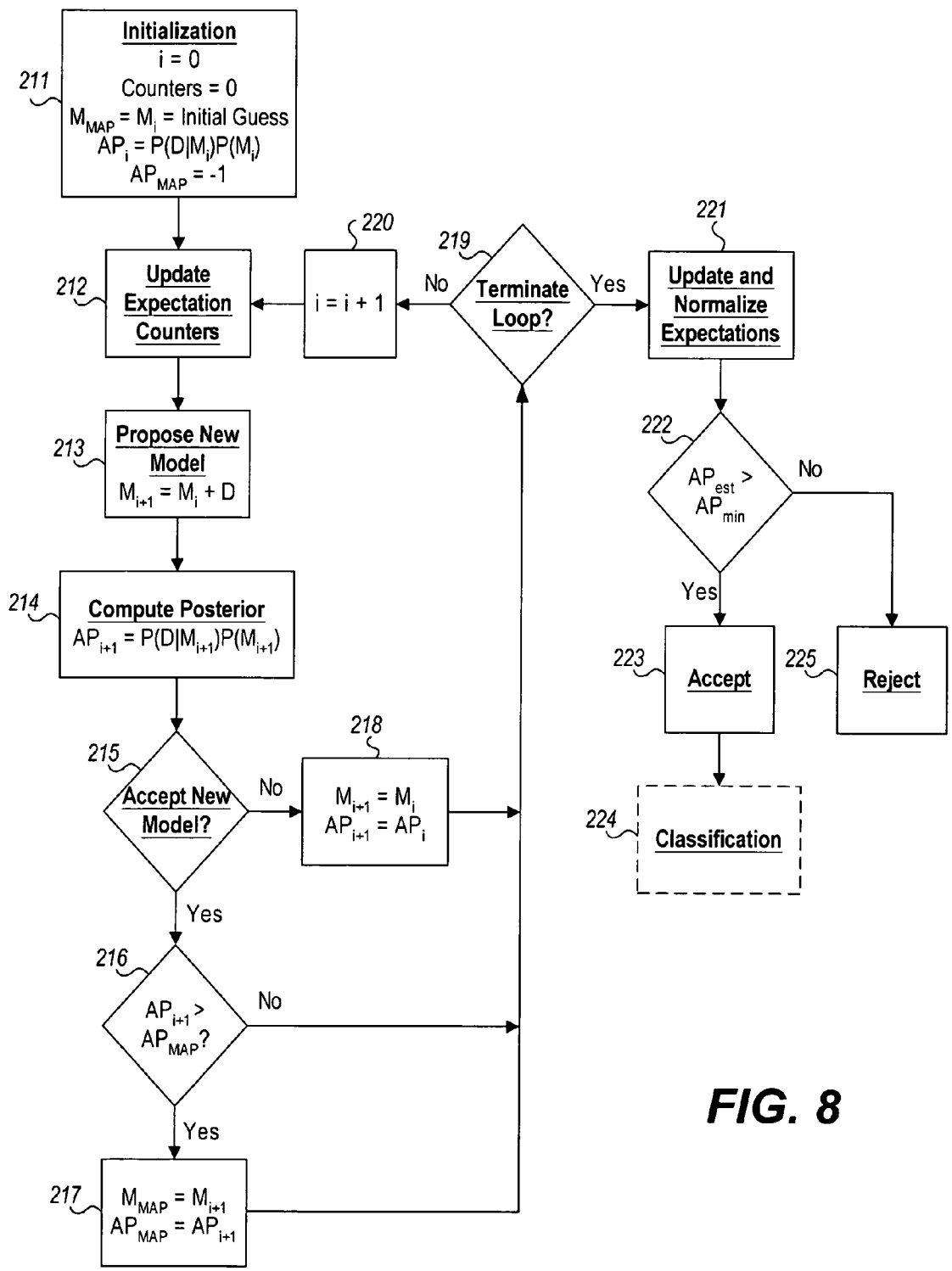
FIG. 8 is an operational flowchart of a preferred embodiment of the estimation technique performed by the reconstruction engine of FIG. 6.

FIG. 8 illustrates in more detail an exemplary operation method 210 for reconstruction engine 120. The method 210 begins with initialization (step 211) of various variables that are used by the reconstruction engine 120. For example, a loop counter i and expectation counters for accumulating expectations $<f_i(M)>$ or histograms are initialized to 0. A starting estimate $M=M_0$, where $M_0$ is an initial guess of the model state of the model M is chosen. While the starting estimate $M=M_0$ can, in principle, be chosen randomly, faster convergence typically results from performing a simple, but less accurate reconstruction, e.g., using tomosynthesis or filtered back projection, and setting the starting estimate to approximate this reconstruction. In the illustrative embodiment, MAP techniques are used to estimate the best fit model $M_{EST}$. Thus, the more general symbol $M_{EST}$ used in FIG. 6 is referred to in FIG. 8 as $M_{MAP}$, where $M_{EST}=M_{MAP}$ in FIG. 6 for this illustration only and not by way of limitation. Accordingly, a MAP estimate $M_{MAP}$ of the model and current model $M_i$ are each set to the starting estimate (i.e., $M_{MAP}=M_i=M_0$). The current posterior $AP_i$ is calculated ($AP_i=P(D|M_i)p(M_i)$), and the posterior of the MAP estimate $AP_{MAP}$ is set to a value indicating that it has not been initialized (e.g., "−1").

If expectations are to be returned by the reconstruction engine 120, expectations $<f_i(M_i)>$ are updated using the current model state (step 212). The expectation counters for accumulating expectations $<f_i(M_i)>$ or histograms are updated with values calculated for the current loop i. For example, if the model state is $M_i$, and the expectation of $f_j(M)$ is desired, add $f_j(M_i)$ to the corresponding counter. For efficiency, counters can be updated only on state changes (and at termination). The expectation counters store the running sum of an associated quantity of interest. When all loop iterations i have completed (after step 219), the expectation counters are updated to reflect the final state, and normalized (step 221), for example by dividing the accumulated sum held by the expectation counter by the number of iterations i to get the normalized expectation values $<f_i(M)>$. A similar strategy works for estimating the posterior P(M|D): in this case a histogram containing a bin for each model state $M_i$ (i=1 to n, where n=number of iterations) is incremented each time the corresponding model state $M_i$ is visited. In the preferred embodiment, Markov Chain Monte Carlo (MCMC) methods are used for visiting model states with frequency proportional to their posterior probability and for approximating the expectations $<f_i(M)>$. It should also be noted that the algorithm 210 may be implemented to execute a number of "warm-up" iterations of the estimate loop (steps 212 through 220) prior to beginning updates of the expectation counters in order prevent skew of the distribution and less accurate expectation values.

Changes to the model are proposed $M_{i+1}=M_i+\Delta$ (step 213), for example by changing the value of one or more of the values of parameters $\pi_{i\_1}, \pi_{i\_2}, \ldots, \pi_{i\_n}$ of $M_i$ (where $M_i=\{\pi_{i\_1}, \pi_{i\_2}, \ldots, \pi_{i\_n}\}$). To this end, a parameter to be altered is chosen, either randomly or sequentially, and a new value is proposed, typically, at random. In some cases, however, it may be possible to sample directly from the posterior or some distribution more nearly resembling it than a purely random choice. When practical, this frequently results in faster equilibration. The posterior of the proposed changed model $M_{i+1}$ is calculated (($AP_{i+1}=P(D|M_{i+1})p(M_{i+1})$)) (step 214), and a determination is then made (step 215) as to whether to accept the model $M_{i+1}$ with the proposed changes.

Figure 9:
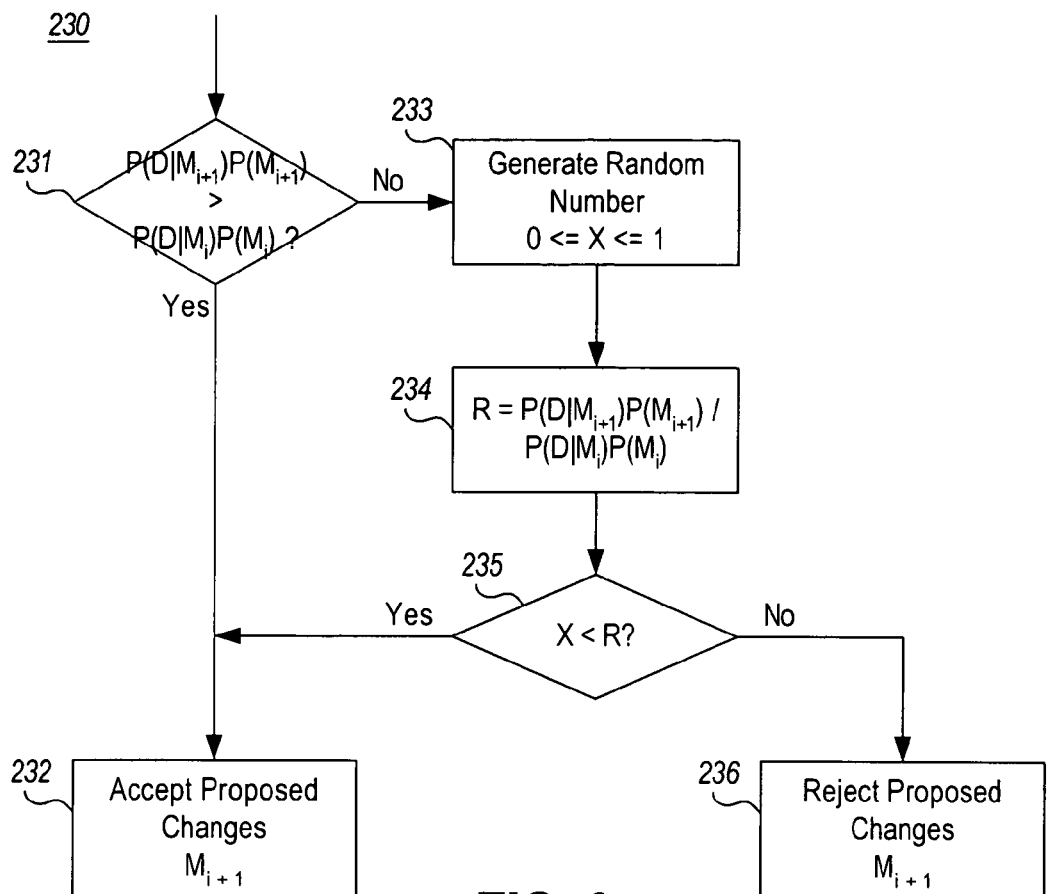
FIG. 9 is an operational flowchart illustrating the Metropolis-Hastings update algorithm used in the preferred embodiment of the algorithm of FIG. 8 for determining whether to accept or reject a given proposed changed model.

Various methods and criteria may be used to determine whether a proposed changed model $M_{i+1}$ should be accepted or rejected. In the preferred embodiment, a Metropolis-Hastings algorithm is used. Other implementations may include, for example only and not by way of limitation, a Gibbs' sampling or simulated annealing. FIG. 9 illustrates an example Metropolis-Hastings update algorithm 230 for determining whether to accept or reject the proposed change to the model. As shown, the posterior $P(D|M_{i+1})P(M_{i+1})$ for the proposed changed model is compared to that for the current model, $P(D|M_i)P(M_i)$ (step 231). If the posterior for the proposed changed model is greater than that for the current model, the change is accepted (step 232).

If the posterior for the proposed changed model is less than or equal to that for the current model, a random number X from 0 to 1 is generated (step 233), and a Hastings' ratio R is calculated as $R=P(D|M_{i+1})P(M_{i+1})/P(D|M_i)P(M_i)$ (step 234). The random number X is compared to the Hastings' ratio R (step 235). If the random number X is less than the Hastings' ratio R, the changes are accepted (step 232), otherwise the changes are rejected (step 236).

Returning to FIG. 8, if the proposed changed model $M_{i+1}$ is accepted (step 215), the reconstruction engine 120 checks to see if the posterior $AP_{i+1}$ of the proposed model $M_{i+1}$ is greater than the current value of the posterior $AP_{MAP}$ of the estimated MAP model $M_{MAP}$ (step 216). If so, the estimated MAP model $M_{MAP}$ and its posterior probability $AP_{MAP}$ are updated to $M_{i+1}$ and $AP_{i+1}$, respectively (step 217).

If, on the other hand, the proposed changed model $M_{i+1}$ is rejected (step 215), the next model state $M_{i+1}$ is set to the current model state $M_i$, thereby effectively discarding the proposed changes, and the proposed model posterior $AP_{i+1}$ is set to the current posterior $AP_i$ (step 218).

Upon completion of steps 216 and/or 217 or 218, a determination is made as to whether the estimation process is finished (step 219). If expectations are computed, one determination is whether the expected values have converged (i.e., are no longer changing to within a desired accuracy, or have estimated variances that are acceptable). Alternatively, especially if expectations are not computed, it may be necessary to stop the computation after a fixed time has elapsed, a fixed amount of computing resources have been used, or a fixed number of iterations have completed. If it has been determined that the estimation process is not yet finished, the loop counter i is updated to i=i+1 (step 220), and the loop including steps 212 through 218 are repeated, iteratively updating any expectation and histogram counters in use, proposing new model $M_{i+1}$ changes, computing the posterior of the proposed changed model $M_{i+1}$, and determining whether or not to accept or reject the changes to the model.

When it has been determined (step 219) that the estimation process is finished, the expectation counters are normalized (step 221), as discussed previously, by dividing the accumulated sums of the counters by the number of iterations i.

The posterior probability $AP_{MAP}$ of the MAP model $M_{MAP}$ is then compared to a minimum threshold, $AP_{min}$, (step 222), and a reject declared (step 225) unless this minimum threshold is exceeded. A reject is declared when the posterior probability is unusually low. Typically, this occurs when the object under inspection differs greatly from that expected. While the above description of a reject decision has been cast in terms of maximum posterior probability, it will be understood that other quantities, such as log posteriors, log likelihoods, or expectations may also be used in a similar manner.

If the minimum threshold, $AP_{min}$, is exceeded, the estimated model, $M_{MAP}$, is accepted (step 223) and one or more of the estimated MAP model $M_{MAP}$, the estimated posterior probability distribution, P(D|M)P(M), or estimated expectations of quantities of interest, <f(M)> are sent to the classification engine 130 (step 224). As described above, the choice of which type of information is sent to he classification engine 130 is dictated by the properties of the posterior distribution and the type of classification engine 130 in use.

For the sake of generality, provision has been made for simultaneous estimation of the MAP model, expectations of features or functions of interest, and of the posterior probability. If one or more of these estimates are not required for classification purposes, it will be understood that corresponding steps in the process may be omitted.

It will be appreciated that in order to meet realtime requirements of automated industrial inspection lines, the operational methods 200, 210, and 230 of FIGS. 7, 8, and 9 respectively are preferably implemented as one or more software routines or applications comprising program instructions tangibly embodied on a storage medium for access and execution by computer hardware. Accordingly, the function blocks of FIG. 6 necessarily comprise hardware and preferably software. In addition, the classification functionality as performed in step 208 of FIG. 7 and step 224 of FIG. 8 may also be implemented as one or more software routines or applications comprising program instructions tangibly embodied on a storage medium for access and execution by computer hardware. The classification functionality of classification engine 130 as performed in step 208 of FIG. 7 and step 224 of FIG. 8 may be combined in the same software application as the algorithm(s) of the reconstruction engine 120, or may be implemented and executed as a separate software routine or application on the same or different computer hardware.

2. Example Application—Inspection of BGA Joint on a PCB

Application of the invention is ideally suited to inspection of solder joints in printed circuit assemblies, especially those solder joints that are arranged in linear, areal, or 3-dimensional arrays. Illustration of a specific embodiment will now be discussed with application to inspection of ball grid array (BGA) joints.

a. Projection Collection

Turning now to the specific illustrative embodiment, FIG. 10A illustrates a schematic diagram of an acquisition apparatus 300 used in accordance with the invention for collecting and analyzing observed projections of an object of interest. In this embodiment, the device under test is a printed circuit board 1 having multiple electronic components 2a, 2b, 2c, 2d, 2e, 2f mounted on the board 1 by way of ball grid array (BGA) joints 10.

FIG. 10B, which is a top view enlargement of a region 383 of the printed circuit board (PCB) 1, more clearly shows the component 2 and BGA joints 10.

The apparatus 300 acquires images, or projections of the BGA joints 10 from a variety of angles. A model of the BGA joints 10 are automatically fitted and evaluated according to the invention.

The image acquisition apparatus 300, as shown in FIG. 10A, comprises an X-ray tube 314 which is positioned in proximity to PCB 1. A fixture 320 supports the PCB 1. The fixture 320 is attached to a positioning table 330 which is capable of moving the fixture 320 and board 1 along three mutually perpendicular axes, X, Y and Z. A rotating X-ray detector 340 comprising a fluorescent screen 350, a first mirror 352, a second mirror 354 and a turntable 356 is positioned in proximity to the circuit board 1 on the side opposite the X-ray tube 314. A camera 358 is positioned opposite mirror 352 for viewing images reflected into the mirrors 352, 354 from fluorescent screen 350. A feedback system 360 has an input connection 362 from a sensor 363 which detects the angular position of the turntable 356 and an output connection 364 to X and Y deflection coils 381 on X-ray tube 314. A position encoder 365 is attached to turntable 356. The position sensor 363 is mounted adjacent encoder 365 in a fixed position relative to the axis of rotation 312. The camera 358 is connected to a master computer 370 via an input line 376. The master computer 370 is connected to a high speed image analysis computer 372. Data is transferred between the master computer 370 and the image analysis computer 372 via data bus 374. An output line 378 from master computer 370 connects the master computer to positioning table 330.

Figure 10C:
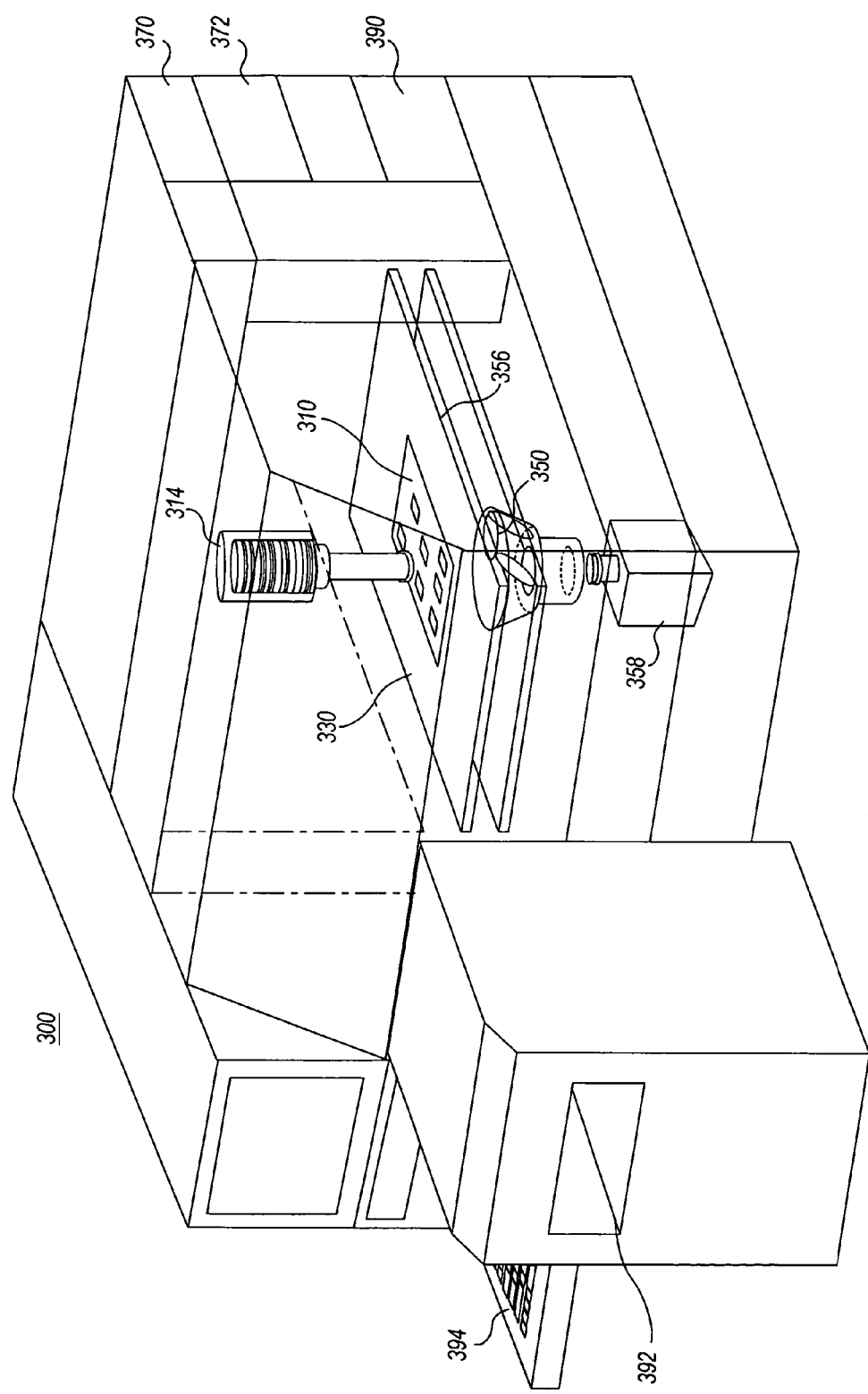
FIG. 10C is a perspective view of the embodiment of the acquisition apparatus of FIG. 10A.

A perspective view of the image acquisition apparatus 300 is shown in FIG. 10C. In addition to the X-ray tube 314, circuit board 1, fluorescent screen 350, turntable 356, camera 358, positioning table 330 and computers 370, 372 shown in FIG. 10A, a granite support table 390, a load/unload port 392 and an operator station 394 are shown. The granite table 390 provides a rigid, vibration free platform for structurally integrating the major functional elements of the apparatus 300, including but not limited to the X-ray tube 314, positioning table 330 and turntable 356. The load/unload port 392 provides a means for inserting and removing circuit boards 1 from the machine. The operator station 394 provides an input/output capability for controlling the functions of the apparatus as well as for communication of inspection data to an operator.

In operation, high resolution, transmission X-ray images of the BGA joints 10 connecting components 2a, 2b, 2c, 2d, 2e, 2f on PCB 1 are acquired by successively varying the position of one or more of the X-ray source 380, detector 350, and/or PCB 1, and acquiring an image (or observed projection $D=d_i$) at each position. Specifically, x-ray tube 314, as shown in FIG. 3A, comprises a cone 315 with an anode 387 and a rotatable electron beam spot 385 which produces a source 380 of X-rays 382. The electron beam spot 385 may be positioned to any location along the circumference of the anode 387 of the cone 315. The X-ray beam 382 illuminates a region 383 of PCB 1 including the BGA joints 10 located within region 383. X-rays 384 which penetrate the BGA joints 10, component 2c and board 1 are intercepted by the rotating fluorescent screen 350.

The position of the fluorescent screen 350 may be varied by rotating the rotatable turntable 356 around axis 312 to various programmed positions. Alignment of the position of the X-ray source 380 with the position of rotatable X-ray detector 340 may be precisely controlled by feedback system 360. The feedback system correlates the position of the turntable 356 with calibrated X and Y deflection values stored in a look-up table (LUT). Drive signals proportional to the calibrated X and Y deflection values are transmitted to the steering coils 381 on the X-ray tube 314. In response to these drive signals, steering coils 381 deflect electron beam 385 to programmed locations on the target anode 387. Master computer 370 controls the positioning of the X-ray source 380 and detector 350, and the acquisition of images at each position. Master computer 370 also controls the movement of positioning table 330 and thus PCB 1 so that different regions of PCB 1 may be automatically positioned within inspection region 383.

X-rays 384 which penetrate the PCB 1 and strike fluorescent screen 350 are converted to visible light 386, thus creating a visible image of region 383 of the PCB 1. The visible light 386 is reflected by mirrors 352 and 354 into camera 358. Camera 358 typically comprises a low light level closed circuit TV (CCTV) camera which transmits electronic video signals corresponding to the X-ray and visible images to the master computer 370 via line 376. The electronic video format image is transferred to the high speed image analysis computer 372 via line 374. Alternatively, the electronic video format image is stored for transport and later analysis by the image analysis computer 372, which may exist separate and/or remote from the image acquisition apparatus 300. The image analysis computer 372 accesses and executes program instructions stored in memory 375 that implement the reconstruction engine 120 and classification engine 130, and includes the highly constrained model M 102, priors P(M) 104, and forward map 110. Execution of these software routines/applications 120, 130 allows the image analysis computer 372 to analyze and interpret the image to determine the quality of the BGA joints 10.

b. Representation of Solder Joints

Figure 11:
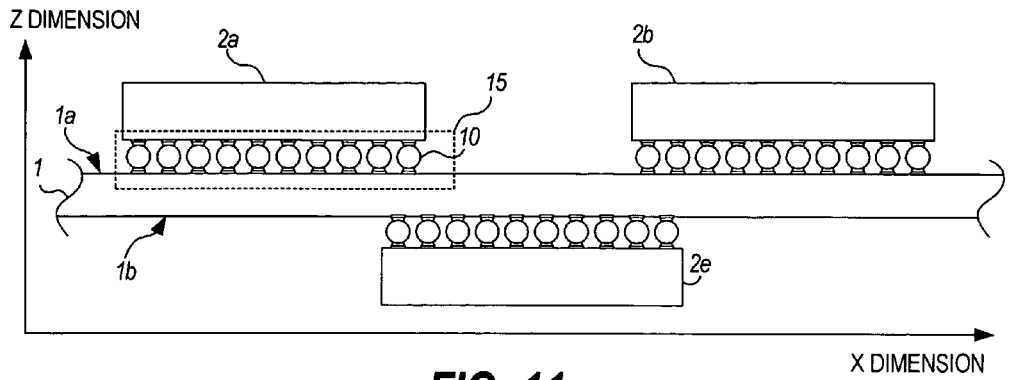
FIG. 11 is a cross-sectional side view of a double-sided printed circuit board (PCB) under inspection, illustrating the x- and z-dimensions.

FIG. 11 depicts a cross-sectional side view of the double-sided printed circuit board (PCB) 1 of FIGS. 10A and 10B in the x- and z-dimensions. Multiple components 2a, 2b, 2c, 2d, 2e, 2f are mounted to each of two exterior surfaces 1a and 1b via ball grid array joints 10 arranged in ball grid arrays 15.

Figure 12:
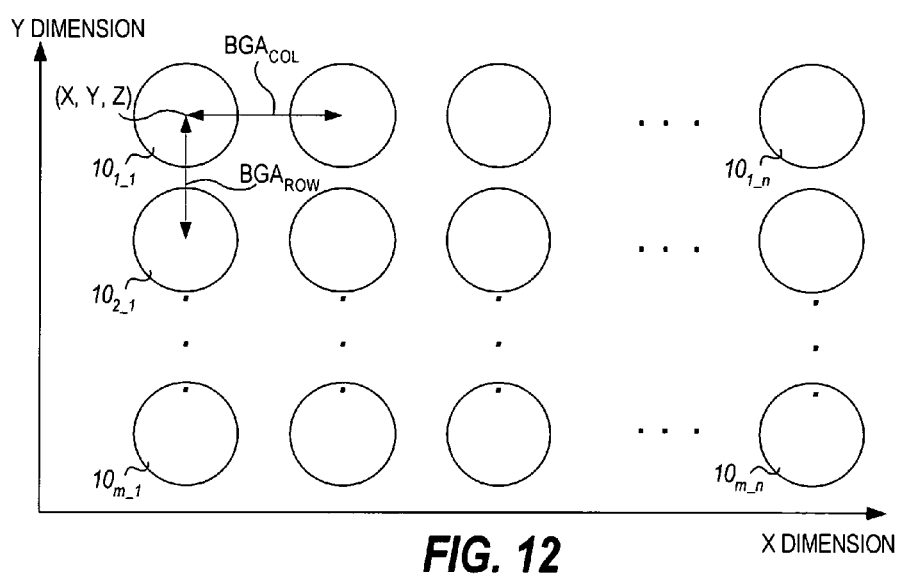
FIG. 12 is a cross-sectional plan view of a ball grid array of a component on the PCB of FIG. 11, illustrating the x- and y-dimensions.

FIG. 12 is a cross-sectional plan view of a ball grid array 15, illustrating the x- and y-dimensions. As illustrated, multiple BGA joints $10_{1\_1}$, $10_{2\_1}$, $10_{m\_1}$, ..., $10_{m\_n}$ are arranged in an areal array, in this example in a set of m rows and n columns. Since the expected row and column spacing of the balls are known in advance, the coordinates of nearby joint centers are not independent (i.e., they are highly correlated).

FIG. 13 is a cross-sectional side view of a single BGA joint 10 in the ball grid array 15, illustrating the x- and z-dimensions. The PCB and IC interface solder fillets 4 and 6 are key areas that need to be examined in order to determine if a good joint is present. As illustrated, the BGA joint 10 may be described as a doubly truncated sphere 5 plus two solder fillets 4 and 6. Thus, the BGA joint may be described by a set of parameters that model a BGA joint 10. For example, the central, spherical portion (i.e., ball) 5 may be parameterized by position x, y, z of the center (three parameters), diameter d (one parameter), and the distance from the center of the ball to the pads which truncate the sphere $s_1$, $s_2$ (two parameters). Similarly maximum radius $r_1$, $r_2$ and wetting angle $\alpha_1$, $\alpha_2$ may be used to parameterize each of the two solder fillets 4 and 6.

The choice of which parameters to use to define the object of interest, in the illustrative embodiment a BGA joint 10, is largely determined by the features that are appropriate for classification of the object of interest. Thus, in the illustrative embodiment where the object of interest is a BGA joint 10, what is needed is a model M having a greatly reduced number of parameters, that allows concise and natural expression of constraints and prior knowledge regarding the joint, and, for use with automated inspection, that provides effective discrimination between acceptable and defective joints. For the BGA joint 10, as illustrated in FIG. 13, discrimination between a good joint and most bad joints can typically be made easily if one could examine any vertical cross section through the joint. For example, FIG. 2 illustrates a BGA joint where the PCB interface fillet 4 that should connect the ball 5 to the PCB pad 3 is missing. Since a vertical cross section at any azimuth angle would typically suffice to detect the missing fillet, this leads naturally to consideration of representations with cylindrical symmetry.

In contrast to a voxel-based representation discussed in the background section, the step of choosing a representation for the highly constrained model M can constrain the range of objects which can be represented, and constitutes a form of prior information, independent of the measured data D. In the illustrative embodiment, the BGA joint objects are directly represented using a small number of parameters (e.g., $M_{BGA} = \{x, y, z, d, s_1, s_2, r_1, r_2, \alpha_1, \alpha_2\}$). Assuming known, homogeneous composition and attenuation properties within each region (e.g. eutectic or high-melting solder for the ball, and eutectic solder for the fillets), the total number of parameters for a BGA joint in this simplified representation is 10, a reduction of more than 300-fold over the voxel-based representation discussed in the background section. As a result of this reduction, the system is no longer ill-conditioned and underdetermined. Faster convergence and fewer problems with local extrema result, as do more sharply peaked, symmetrical posterior distributions.

For simplicity, the above description has been in terms of a single joint. It is typically desirable to simultaneously analyze regions containing multiple joints, for example the entire ball grid array 15 of a component 2 in FIG. 12. In this representation, highly constrained parameterization is achieved by simply including parameters for each joint. Depending on the situation, parameters for nearby joints may or may not be chosen to be independent. For the independent case, the reduction in parameters is identical to that achieved in the single joint case. With shared or highly correlated parameters, such as in an array of theoretically identical joints (e.g., a BGA), even greater reductions are possible. For example, in a BGA array illustrated in FIG. 12, additional parameters may be defined to eliminate having to define independent BGA parameters for each of the BGA joints in the array. BGA joint spacing is usually known to within small tolerances as provided by the manufacturer specifications, which means that the x and y coordinates for neighboring balls 5 are highly correlated (i.e., the prior probability for a ball 5 being the correct spacing from its neighbors is very high, and that for being, for example three times the normal spacing away is essentially zero). Similarly, there are gentle variations in the z coordinate across a part (due mostly to board and component warp), but the z coordinates are normally highly correlated.

Of course, it will be appreciated by those skilled in the art that many alternative formulations are possible. An ellipsoid might be used in place of a sphere for a BGA joint, for example. Additionally, some users may wish to detect the presence of any voids (gas bubbles) in the fillet regions. Each void may be simply parameterized (e.g., as a truncated ellipsoid). The number of voids, however, represents a hyper-parameter that will generally not be known in advance. In ML or MAP estimation, hyper-parameters are generally handled by trying possible values for the hyper-parameter, and then using a criterion such as the Akaike or Bayes Information Criteria (AIC or BIC, respectively) to compare models of varying complexity. When full Bayesian inference is used, however, hyper-parameters may be fitted directly by defining an additional prior over their values and then using reversible-jump Markov Chain Monte Carlo to estimate expectations.

In addition to the joint(s) in question, projections are affected by the PCB and component substrates and by joints and components on the other side (or at different layers) of the board. The PCB itself will typically have known composition (e.g., FR-4) and thickness, with pads and traces whose layout is known in advance from CAD data. A small number of additional parameters may be used to represent information such as whether or not particular vias are filled with solder. Similarly, components on the opposite side (or in various layers) may be represented either as another highly constrained representation with a small number of adjustable parameters (preferred), or as a fixed model representing the nominal case. In either case, failure to attain a sufficiently high maximum (for MAP estimation) or average (for MCMC) posterior probability, P(M|D), can be used as a "reject" situation in which the fitted model does not agree well with the measured projections. In the BGA example, highly asymmetrical defects, e.g. narrow solder bridges, cannot be directly expressed in our representation, and are likely to cause rejects.

c. Defining the Prior Probabilities p(M)

Defining the set of prior probabilities, p(M), for possible instances of the object of interest may be done in several ways. In the parametric representation of the illustrative example, where M is modeled by the parameters $M_{BGA} = \{x,$ y, z, d, $s_1$, $s_2$, $r_1$, $r_2$, $\alpha_1$, $\alpha_2\}$, a probability density function $P(M_{BGA})$ is defined for the joint distribution. Alternatively, the "naive Bayes" approach may be used in which the parameters are treated independently.

Prior probabilities p(M) may be assigned by theoretical calculation, by statistical sampling of representative regions, and/or from expert knowledge. For example, in the illustrative embodiment, suppose the manufacturer specification sheet for the BGA balls define the diameter of the ball to be 0.030+/−0.002 inches in diameter. If the ball is a "non-collapsible" BGA (where the ball itself doesn't melt during soldering), then the diameter d that one would expect to see on the finished board is very nearly this value. Thus, one might, for example, assume a Gaussian distribution using a mean μ=0.030 and standard deviation σ=002. Thus, $$P(m_i = r) = \frac{1}{\sigma\sqrt{2\pi}} e^{-\frac{1}{2}(\frac{x-\mu}{\sigma})}$$

Collapsible BGAs are more common. In this case, the diameter d can change during soldering. One way to address this situation is to use the starting diameter d only as a rough guide. Not only will the standard deviation a be wider, but the mean μ may shift during soldering. In this case, the prior distribution may be developed from statistical sampling of actual measurements (X-ray, optical, or from physically cross-sectioning sample joints) of the joints, or previous experience with similar joints. Finally, the prior distribution P(d) should include the entire range of circumstances one would expect to encounter. For example, missing BGA balls do occur, albeit rarely, so the prior distribution for the diameter of the ball should allow for this possibility by extending all the way down to 0. Similarly, bulk shorts where several adjacent balls are shorted together by a glob of excess solder also can occur. Therefore, the prior distribution for ball diameter should extend up to the center-center distance. Typically, one would define a distribution which peaks near the expected value, and which decreases gradually over the desired range. In extreme cases where little or no prior information about how likely a given value is for a particular parameter, an "uninformative prior" (e.g., a uniform distribution over the range) is used.

Similar considerations are applied to every model parameter. In summary, the prior probability P(p) of a given parameter p∈(x, y, z, d, $s_1$, $s_2$, $r_1$, $r_2$, $\alpha_1$, $\alpha_2$) is defined by one or more of the following considerations: 1) expert or manufacturer information, 2) experimental characterization of the distribution (i.e., statistical sampling, or 3) non-informative priors. The use of a non-informative prior for the prior probability of a parameter is not as unhelpful as its name suggests, since strong prior knowledge is implicit in the choice of model M representation.

d. The Forward Map

The invention also requires a detailed forward map for calculating the likelihood, $P(D=d_i|M=m_i)$, of obtaining a given set $D=d_i$ of projections from a particular instance $M=m_i$ of the model. A simple way to compute likelihoods is to convert from the high-level parametric representation to a low-level representation, e.g., a voxel-based representation, to then perform either deterministic ray-tracing or ray-tracing with some of the stochastic components such as scattering included, and, finally, to treat any remaining uncertainties and errors as additive noise. Conceptually, it is possible to directly compute a map from the high-level parametric model to the corresponding projections; however, in the illustrative embodiment, the parametric model M may be readily translated into either (by way of example only and not limitation) a volumetric or surface patch model or other appropriate representation, for purposes of performing computational ray-tracing.

In order to accurately represent the forward model, one must incorporate the noise process into the forward model. Several likely sources of error exist, including error due to scattering, uncertainties in attenuation coefficient, measurement geometry (such a uncertainty in the spot position and size, pixel array placement and spatial sensitivity), noise in the radiation source, and in the response of the detector array (which show up as changing X-ray intensity and pixel sensitivity over time and also as random variation for otherwise apparently identical measurements). For the purposes of the forward map, noise may be defined as not only measurement noise or repeatability problems, but as any difference between the predicted projection and the observed projection. The noise function can be determined through measurement, simulation, modeling, or combinations thereof. Typically expert knowledge is combined with experimental measurements of noise using known test objects. Often a suitable parametric model closely approximating the actual noise can be found. Gaussian, Poisson, and uniform distributions are frequently used, for example.

The noise process N can be quantified by repeated measurement of a known test object (or objects) under identical, realistic, measurement conditions. This corresponds to sampling from the distribution P(D|M) for a fixed model, $M_i$. If K( ) denotes the forward map P(D|M), then D=K(M)+N. Therefore, each measurement gives the noise sample $n_i=d_i-K(m_i)$ from the noise distribution N, because $M=m_i$ and forward map K=P(D|M) are known. Since the forward map K is used in the difference $d_i-K(m_i)$ the noise sample $n_i$ also contains any modeling errors. As a result, changes in model representation or the forward map can alter the noise distribution. If the sampling grid is fine enough, a sampled version of the noise probability density function N may be used directly. More typically, the noise process can be modeled and the samples used to fit some appropriate parametric distribution.

Simulation may also be used to include stochastic components directly, rather than modeling them as additive noise. To simulate scattering, for example, one might perform a Monte Carlo simulation in which photons have a small probability of changing direction or energy at each interaction. Monte Carlo simulation can be computationally expensive for inclusion in the forward map. One possibility is to perform suitable simulations offline, summarizing the results in either parametric or non-parametric form for use in the forward map.

e. Estimating the Model $M_{EST}$ of the Imaged BGA Joint

Given the highly constrained model $M_{BGA}=\{x, y, z, d, s_1, s_2, r_1, r_2, \alpha_1, \alpha_2\}$, the set of priors $P(M_{BGA})$, forward map, and set of projections D, the reconstruction engine 120 estimates a model $M_{EST}$ that best fits the projections D. In the preferred embodiment, the methods described in FIGS. 7, 8, and 9 are used. Preferably, expectation values are calculated for use as the basis of classification of the imaged BGA joint.

f. BGA Joint Classification

In the preferred embodiment, expectation values for features of interest of the imaged BGA joint are used as the basis for classifying an imaged BGA joint (or array of joints). For example, mean values of the features describing a joint are often preferable to the MAP estimates, particularly when the posterior distribution is highly skewed. Expectations of other quantities (e.g. volume or other functions of the features) can be useful for classification.

Figure 14:
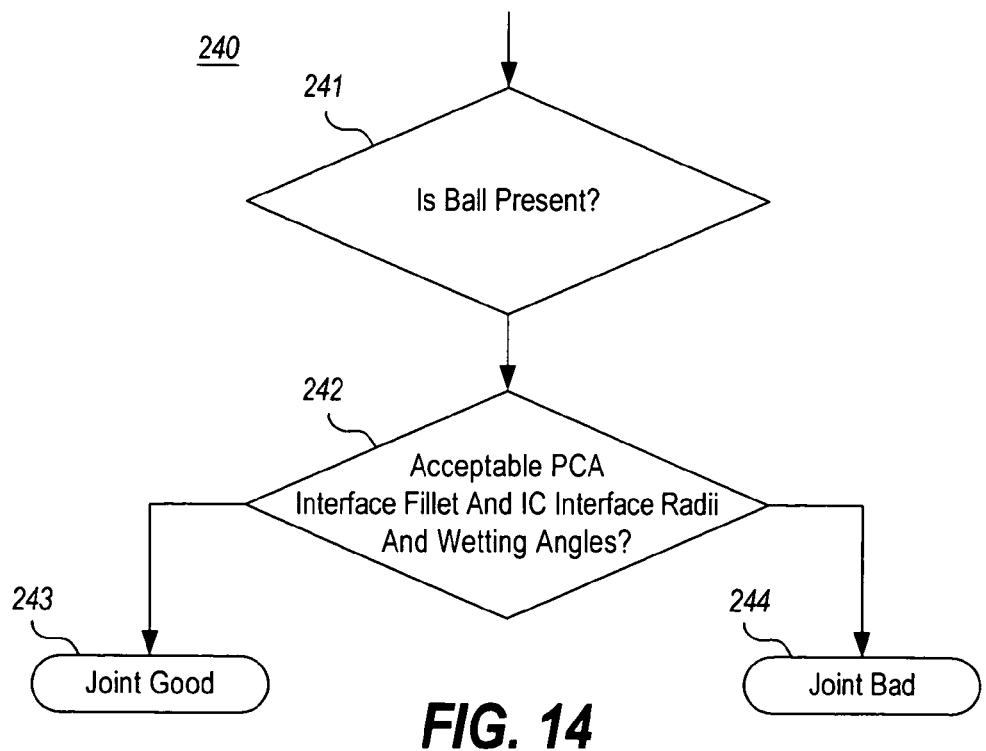
FIG. 14 is an operational flowchart illustrating one embodiment of a classification method for a BGA joint in accordance with the invention.

FIG. 14 shows a simple classifier 240 in which: if the BGA ball is present (step 241), and if both PCB and integrated circuit interface fillets 4 and 6 have acceptable radii and wetting angles (step 242), then the joint is classified as good (step 243); otherwise the joint is classified as bad (step 244). Additional criteria (e.g., voids are not present at the PCB or integrated circuit interface) may be readily incorporated. As described above, while either expectations or MAP estimates of these parameters can be used for classification, the former are more robust when the posterior distribution. happens to be broad and asymmetrical.

The classification engine 130, in this illustrative embodiment embodied as classifier algorithm 240, is preferably implemented as one or more software routines or applications comprising program instructions tangibly embodied on a storage medium for access and execution by computer hardware.

3. Summary

In summary, many advantages derive from use of a highly constrained model M. First, because the dimensionality of the problem is greatly reduced (e.g., a significant reduction in parameters), convergence is much more rapid. As described above, additional performance gains can be achieved by incorporating multi-resolution method in either MAP or MCMC estimation. Second, the number of parameters has been reduced significantly, so that in many cases the problem is now over—rather than under-determined. This often leads to a single global optimum, with local extreme no longer a concern, and unwanted artifacts in the reconstruction reduced or eliminated. An additional side effect is that the posterior probability, P(M|D), may now be sufficiently peaked so that use of MAP estimation can be justified in some cases. Nevertheless, MCMC estimation is preferred for its greater applicability when time and computational resources permit. Finally, well-chosen parameters typically lend themselves naturally to automated classification.

Although the invention has been presented by application to a BGA joint or arrays of BGA joints, similar considerations apply to column grid array (CGA) joints, plated through holes (PTH), surface mount pin grid arrays (SMPGA) and other joint types which are not shown. In addition to their symmetrical 3-dimensional nature, these joint types are also typically deployed in dense arrays (linear, areal, or even 3-dimensional) with large numbers of similar joints in close proximity.

Although this preferred embodiment of the present invention has been disclosed for illustrative purposes, those skilled in the art will appreciate that various modifications, additions and substitutions are possible, without departing from the scope and spirit of the invention as disclosed in the accompanying claims. It is also possible that other benefits or uses of the currently disclosed invention will become apparent over time.

What is claimed is:

1. A method for automated industrial inspection of manufactured devices characterized by a repetitive array of similar objects, comprising:

obtaining a set of observed projections of one or more objects under inspection that are members of said repetitive array;

obtaining a highly constrained model of said objects under inspection based partially on or expressing some prior information about said objects under inspection;

obtaining a distribution or density expressing prior probabilities, p(M), for all possible instances of said objects under inspection representable by said highly constrained model;

obtaining a forward map capable of predicting the likelihood of observing specified projections that would result from any collection of objects representable by said highly constrained model;

estimating a model of said objects under inspection based on said set of observed projections, said highly constrained model, said distribution or density expressing prior probabilities, and said forward map.

2. The method of claim 1, further comprising:
classifying said objects under inspection based on said estimated model of said objects under inspection.

3. The method of claim 1, wherein said step for estimating said model further comprises:
finding a maximum a posteriori (MAP) estimate of said objects under inspection.

4. The method of claim 3, further comprising:
classifying said objects under inspection based on said MAP estimate.

5. The method of claim 1, wherein said step for estimating said model further comprises:
determining a posterior probability density or distribution of said objects under inspection.

6. The method of claim 5, wherein said step for determining said posterior probability density or distribution comprises:
utilizing Bayesian techniques to determine said posterior probability density or distribution given said set of observed projections.

7. The method of claim 5, further comprising:
classifying said objects under inspection based on said posterior probability density or distribution.

8. The method of claim 1, wherein said step for estimating said model further comprises:
calculating expectations of one or more features comprising said highly constrained model or functions thereof.

9. The method of claim 8, further comprising:
classifying said objects under inspection based on said expectations of said one or more features.

10. The method of claim 8, wherein said calculating step comprises:
implementing a Markov Chain Monte Carlo (MCMC) algorithm to visit model states with frequency proportional to their posterior probability and to approximate said expectations of said one or more features.

11. The method of claim 1, wherein said method for estimating said model comprises:
initializing a current model to an initial estimate;
computing a posterior of said current model to generate a current model posterior;
proposing changes to said current model to generate a next model;
computing a posterior of said next model to generate a next model posterior;
determining whether to accept or reject said next model based on values of said current model posterior and said next model posterior;
if said next model is to be accepted, updating said estimated model with said next model, and if said next model is to be rejected, discarding said proposed changes to said current model; and repeating said proposing step through said updating or said discarding steps until sufficient accuracy is achieved or allotted time and/or iterations have expired.

12. A method in accordance with claim 11, wherein said step for determining whether to accept or reject said next model comprises:
utilizing a Metropolis-Hastings algorithm.

13. The method of claim 1, wherein:
said repetitive array of similar objects comprises an array of electrical connections in an electronic assembly.

14. The method of claim 13, wherein said array of electrical connections comprises an array of integrated circuit joints.

15. The method of claim 1, further comprising:
generating said observed projections using penetrating radiation.

16. The method of claim 15, wherein:
said penetrating radiation comprises X-rays.

17. The method of claim 1, wherein:
said step for estimating said model of said objects under inspection is performed in realtime.

18. A computer readable storage medium tangibly embodying program instructions implementing a method for automated industrial inspection of manufactured devices characterized by a repetitive array of similar objects, the method comprising the steps of:

obtaining a set of observed projections of one or more objects under inspection that are members of said repetitive array;

obtaining a highly constrained model of said objects under inspection based partially on or expressing some prior information about said objects under inspection;

obtaining a distribution or density expressing prior probabilities, p(M), for all possible instances of said objects under inspection representable by said highly constrained model;

obtaining a forward map capable of predicting the likelihood of observing specified projections that would result from any collection of objects representable by said highly constrained mode;

estimating a model of said objects under inspection based on said set of observed projections, said highly constrained model, said distribution or density expressing prior probabilities, and said forward map.

19. The computer readable storage medium of claim 18, further comprising:
classifying said objects under inspection based on said estimated model of said objects under inspection.

20. The computer readable storage medium of claim 18, wherein said step for estimating said model further comprises:
finding a maximum a posteriori (MAP) estimate of said objects under inspection.

21. The computer readable storage medium of claim 20, further comprising:
classifying said objects under inspection based on said MAP estimate.

22. The computer readable storage medium of claim 18, wherein said step for estimating said model further comprises:
determining a posterior probability density or distribution of said objects under inspection.

23. The computer readable storage medium of claim 22, wherein said step for determining said posterior probability density or distribution comprises:
utilizing Bayesian techniques to determine said posterior probability density or distribution given said set of observed projections.

24. The computer readable storage medium of claim 22, further comprising:
classifying said objects under inspection based on said posterior probability density or distribution.

25. The computer readable storage medium of claim 18, wherein said step for estimating said model further comprises:
calculating expectations of one or more features comprising said highly constrained model or functions thereof.

26. The computer readable storage medium of claim 25, further comprising:
classifying said objects under inspection based on said expectations of said one or more features.

27. The computer readable storage medium of claim 25, wherein said calculating step comprises:
implementing a Markov Chain Monte Carlo (MCMC) algorithm to visit model states with frequency proportional to their posterior probability and to approximate said expectations of said one or more features.

28. The computer readable storage medium of claim 18, wherein said method for estimating said model comprises:
initializing a current model to an initial estimate;
computing a posterior of said current model to generate a current model posterior;
proposing changes to said current model to generate a next model;
computing a posterior of said next model to generate a next model posterior;
determining whether to accept or reject said next model based on values of said current model posterior and said next model posterior;
if said next model is to be accepted, updating said estimated model with said next model, and
if said next model is to be rejected, discarding said proposed changes to said current model; and
repeating said proposing step through said updating or said discarding steps until sufficient accuracy is achieved or allotted time and/or iterations have expired.

29. A computer readable storage medium in accordance with claim 28, wherein said step for determining whether to accept or reject said next model comprises:
utilizing a Metropolis-Hastings algorithm.

30. The computer readable storage medium of claim 18, wherein:
said repetitive array of similar objects comprises an array of electrical connections in an electronic assembly.

31. The computer readable storage medium of claim 30, wherein said array of electrical connections comprises an array of integrated circuit joints.

32. The computer readable storage medium of claim 18, wherein:
said step for estimating said model of said objects under inspection is performed in realtime.

33. An automated imaging inspection system for automated industrial inspection of manufactured devices characterized by a repetitive array of similar objects, said system comprising:
a reconstruction engine responsive to receiving a set of observed projections of one or more objects under inspection that are members of said repetitive array by estimating a model of said objects under inspection based on said set of observed projections, a highly constrained model of said objects under inspection based partially on or expressing some prior information about said objects under inspection, a prior probability distribution or density expressing prior probabilities for all possible instances of said object representable by said highly constrained model, and a forward map capable of predicting the likelihood of observing specified projections that would result from any collection of objects representable by said highly constrained model.

34. The system of claim 33, further comprising:
a classification function which classifies said objects under inspection based on said estimated model of said objects under inspection.

35. The system of claim 33, wherein said reconstruction engine comprises:
a maximum a posteriori (MAP) algorithm which operates to find a maximum a posteriori (MAP) estimate of said objects under inspection.

36. The system for claim 35, further comprising:
a classification function which classifies said objects under inspection based on said MAP estimate.

37. The system of claim 33, wherein said reconstruction engine comprises:
an algorithm which determines a posterior probability density or distribution of said objects under inspection.

38. The system for claim 37, wherein:
said algorithm which determines said posterior probability density or distribution of said objects under inspection comprises:
a Bayesian estimation algorithm which determines said posterior probability density or distribution given said set of observed projections.

39. The system of claim 37, further comprising:
a classification function which classifies said objects under inspection based on said posterior probability density or distribution.

40. The system of claim 33, wherein said reconstruction engine comprises:
an algorithm which calculates expectations of one or more features comprising said highly constrained model or functions thereof.

41. The system of claim 40, further comprising:
a classification function which classifies said objects under inspection based on said expectations of said one or more features.

42. The system of claim 40, wherein said algorithm which calculates expectations comprises:
a Markov Chain Monte Carlo (MCMC) algorithm which visits model states with frequency proportional to their posterior probability and to approximate said expectations of said one or more features.

43. The system of claim 33, wherein:
said repetitive array of similar objects comprises an array of electrical connections in an electronic assembly and said object comprises a single electrical connection that is a member of said array of electrical connections.

44. The system of claim 43, wherein said array of electrical connections comprises an array of integrated circuit joints.

45. The system of claim 33, wherein:
said repetitive array of similar objects comprises an array of electrical connections in an electronic assembly and said object comprises two or more electrical connections that are members of said array of electrical connections.

46. The system of claim 45, wherein said array of electrical connections comprises an array of integrated circuit joints.

47. The system of claim 33, further comprising:
a projection collector which collects said set of observed projections of said objects under inspection.

48. The system of claim 47, wherein:
said projection collector generates said observed projections using penetrating radiation.

49. The system of claim 48, wherein:
said penetrating radiation comprises X-rays.

50. The system of claim 33, wherein:
said reconstruction engine estimates said model of said objects under inspection in realtime.

51. An automated imaging inspection system for automated industrial inspection of electrical connections arranged in a repetitive array in an electronic assembly, said system comprising:
a reconstruction engine which receives a set of observed projections of one or more electrical connections under inspection in a repetitive array of an electronic assembly under inspection, said reconstruction engine comprising:
a reconstruction algorithm which receives said set of observed projections and estimates one or more of:
a maximum a posteriori (MAP) estimate of said one or more electrical connections under inspection;
a posterior probability density or distribution of said one or more electrical connections under inspection;
one or more expectations of one or more features comprising said highly constrained model or functions thereof;
wherein said reconstruction algorithm utilizes:
a highly constrained model of said one or more electrical connections under inspection based partially on or expressing some prior information about said one or more electrical connections;
a prior probability distribution or density expressing prior probabilities for all possible instances of said one or more electrical connections under inspection representable by said highly constrained model; and
a forward map capable of predicting the likelihood of observing said set of observed projections that would result from any collection of said one or more electrical connections representable by said highly constrained model.

52. The system of claim 51, further comprising:
a classification function which classifies said one or more electrical connections under inspection based on said MAP estimate.

53. The system of claim 51, further comprising:
a classification function which classifies said one or more electrical connections under inspection based on said posterior probability density or distribution.

54. The system of claim 51, further comprising:
a classification function which classifies said one or more electrical connections under inspection based on said expectations of said one or more features.

55. The system of claim 51, further comprising:
a projection collector which collects said set of observed projections of said one or more electrical connections under inspection.

56. The system of claim 55, wherein:
said projection collector generates said observed projections using penetrating radiation.

57. The system of claim 56, wherein:
said penetrating radiation comprises X-rays.

58. The system of claim 51, wherein:
said reconstruction engine estimates said model of said one or more electrical connections under inspection in realtime.

* * * * *

UNITED STATES PATENT AND TRADEMARK OFFICE
CERTIFICATE OF CORRECTION

PATENT NO. : 7,099,435 B2
APPLICATION NO. : 10/714321
DATED : August 29, 2006
INVENTOR(S) : Heumann et al.

It is certified that error appears in the above-identified patent and that said Letters Patent is hereby corrected as shown below:

On Title Page, in field (56), under "Other Publications", delete "Technology" and insert -- Tomography --, therefor.

On Title Page, in field (56), under "Other Publications", after "Optimal" insert -- . --.

On Title Page, in field (56), under "Other Publications", delete "German" and insert -- Geman --, therefor.

On Title Page, in field (56), under "Other Publications", delete "Proton" and insert -- Photon --, therefor.

On Title Page, in field (56), under "Other Publications", delete "Herbert" and insert -- Hebert --, therefor.

In column 20, line 38, in Claim 18, delete "mode" and insert -- model --, therefor.

In column 22, line 51, in Claim 43, delete "obiect" and insert -- object --, therefor.

In column 22, line 57, in Claim 45, delete "obiects" and insert -- objects --, therefor.

In column 22, line 59, in Claim 45, delete "obiect" and insert -- object --, therefor.

In column 22, line 67, in Claim 47, delete "proiections" and insert -- projections --, therefor.

UNITED STATES PATENT AND TRADEMARK OFFICE
CERTIFICATE OF CORRECTION

PATENT NO.       : 7,099,435 B2
APPLICATION NO.  : 10/714321
DATED            : August 29, 2006
INVENTOR(S)      : Heumann et al.

It is certified that error appears in the above-identified patent and that said Letters Patent is hereby corrected as shown below:

In column 22, line 67, in Claim 47, delete "obiects" and insert -- objects --, therefor.

Signed and Sealed this

Twenty-sixth Day of December, 2006

JON W. DUDAS
*Director of the United States Patent and Trademark Office*